US010383619B2

(12) United States Patent
Thal

(10) Patent No.: US 10,383,619 B2
(45) Date of Patent: Aug. 20, 2019

(54) MODIFIED ADJUSTABLE, LOCKING ALL-SUTURE ANCHOR ASSEMBLY AND METHOD FOR REPAIR

(71) Applicant: Raymond Thal, McLean, VA (US)

(72) Inventor: Raymond Thal, McLean, VA (US)

( * ) Notice: Subject to any disclaimer, the term of this patent is extended or adjusted under 35 U.S.C. 154(b) by 0 days.

(21) Appl. No.: 15/460,655

(22) Filed: Mar. 16, 2017

(65) Prior Publication Data

US 2017/0290578 A1 Oct. 12, 2017

Related U.S. Application Data

(60) Provisional application No. 62/319,029, filed on Apr. 6, 2016.

(51) Int. Cl.
*A61B 17/04* (2006.01)

(52) U.S. Cl.
CPC .. *A61B 17/0401* (2013.01); *A61B 2017/0403* (2013.01); *A61B 2017/044* (2013.01); *A61B 2017/0406* (2013.01); *A61B 2017/0409* (2013.01); *A61B 2017/0414* (2013.01)

(58) Field of Classification Search
CPC ........ A61B 17/0401; A61B 2017/0403; A61B 2017/0406; A61B 2017/0409; A61B 2017/0414; A61B 2017/044
See application file for complete search history.

(56) References Cited

U.S. PATENT DOCUMENTS

| | | | | |
|---|---|---|---|---|
| 2007/0185532 A1* | 8/2007 | Stone | ................. | A61B 17/0401 606/232 |
| 2009/0062847 A1* | 3/2009 | Ken | .................. | A61B 17/0057 606/213 |
| 2011/0270278 A1* | 11/2011 | Overes | ............... | A61B 17/0057 606/144 |
| 2012/0197271 A1* | 8/2012 | Astorino | ............ | A61B 17/0057 606/148 |
| 2012/0290004 A1* | 11/2012 | Lombardo | ......... | A61B 17/0401 606/232 |
| 2013/0110165 A1* | 5/2013 | Burkhart | ............ | A61B 17/0401 606/232 |
| 2013/0296934 A1* | 11/2013 | Sengun | .............. | A61B 17/0401 606/232 |
| 2014/0081325 A1* | 3/2014 | Sengun | .............. | A61B 17/0401 606/232 |

* cited by examiner

Primary Examiner — Jocelin C Tanner
(74) Attorney, Agent, or Firm — Welsh Flaxman & Gitler LLC

(57) ABSTRACT

An adjustable, locking all-suture anchor assembly includes at least one suture strand and an all-suture anchoring element. The suture strand has a suture first end and a suture second end, wherein the suture first end includes an enlarged capturable structure and the suture second end is free and accessible for manipulation by a medical practitioner. In use, the suture first end is held in or by the all-suture anchoring element through inclusion of the enlarged capturable structure and the enlarged capturable structure functions to anchor the suture first end in relation to the all-suture anchoring element and retain the suture first end in position relative to the all-suture anchoring element when the suture second end is pulled.

7 Claims, 10 Drawing Sheets

MODIFIED ADJUSTABLE, LOCKING ALL-SUTURE ANCHOR ASSEMBLY AND METHOD FOR REPAIR

CROSS REFERENCE TO RELATED APPLICATION

This application claims the benefit of U.S. Provisional Patent Application Ser. No. 62/319,029, entitled "MODIFIED ADJUSTABLE, LOCKING ALL-SUTURE ANCHOR ASSEMBLY AND METHOD FOR REPAIR ALL-SUTURE KNOTLESS REPAIR SYSTEM," filed Apr. 6, 2016.

BACKGROUND OF THE INVENTION

1. Field of the Invention

The present invention relates to devices or methods used in tissue repair, and more particularly to an adjustable, locking all-suture anchor assembly and a method for attachment of biological tissue (i.e., tendons or ligaments) to a bone mass.

2. Description of the Related Art

Soft tissues, such as tendons and ligaments, generally are attached to bone by small collagenous fibers. These connections are strong but permit the tendons and ligaments to be flexible. When a tissue, or a portion of a tissue, is torn away from the bone and requires repair, a surgeon is often required to repair the detached soft tissue with sutures, which are passed through bone tunnels and tied. A number of devices have been developed for securing a ligament or tendon to a bone mass. These devices can be used in place of bone tunneling techniques. These attachment devices are usually applied through extensive surgical incisions and, in some circumstances, by arthroscopic surgical techniques. The placement of bone tunnels for repair can be difficult and generally requires large open incisions. Through the advent of arthroscopic surgery, where the surgeon looks into a joint cavity with an arthroscope, there has been a trend to repair soft tissues back to bone through small incisions called portals.

A variety of devices are available for attaching objects to bone, such as screws, staples, suture anchors, and sutures alone. These devices have been used to attach soft tissue, such as ligaments, tendons, muscles to bone. A suture anchor assembly is a device, which utilizes small anchors, including those made of suture material alone, with additional suture materials attached thereto. A device, such as a screw, is inserted into the bone mass and anchored in place. After insertion of the anchor device, the attached suture is passed through the tissue to be repaired. The tying of a knot in the suture is then required to secure the tissue to the bone. The process of passing the anchored suture through the soft tissue and tying a knot is time consuming and difficult to undertake in the tight space encountered during arthroscopic surgery and sometimes even in conventional open surgery.

Knotless anchor assemblies have been popular and are embodied in a number of prior patents such as U.S. Pat. No. 5,709,708 wherein there is provided an assembly with an anchor means having a snag means and a loop suture element attached thereto. The suture loop is passed through the tissue to be repaired. The snag means then captures the loop suture element. The anchor is then inserted into a drill hole in a bone mass and the anchor locks into the bone. As the anchor is inserted into the drill hole, the tissue is pulled into secure attachment with a bone mass.

Further, in U.S. Pat. No. 6,045,574 there is provided an assembly with an anchor means having a snag means, and a hollow sleeve element with a loop suture element attached thereto. The snag means captures a loop suture element of the hollow sleeve element to draw tissue into secure attachment with a bone mass.

Further, there is provided an all-suture anchor assembly, such as disclosed in U.S. Patent Application Publication No. 2012/0290004 having an all fibrous construct, which is incorporated by reference. The device requires the tying of a knot to complete the surgical repair.

However, difficulties still exist with the all-suture anchor assembly and the present invention attempts to address these with a method and apparatus for adjustable, knotless anchoring using an all-suture anchor assembly.

SUMMARY OF THE INVENTION

It is, therefore, an object of the present invention to provide a modified adjustable, locking all-suture anchor assembly that does not require the tying of a knot. The adjustable, locking all-suture anchor assembly is composed of a suture strand with an all-suture anchoring element holding one end of the suture strand via a knot, enlargement or bead and enabling passing of the other end of the suture strand through the all-suture anchoring element. One end of the suture strand is threaded through the all-suture anchoring element for completion of a tissue repair. The all-suture anchor assembly after threading of the one end of the suture strand through the all-suture anchoring element allows for the end which has been passed through the anchoring element to be pulled thereby drawing the tissue to the bone to effectuate a repair. The suture strand(s) may thereby have its length for a repair adjustable in size.

It is also an object of the present invention to provide a modified adjustable, locking all-suture anchor assembly wherein the suture strand(s) that is attached to or used with the all-suture anchoring element has a knot, barbs, beads, or capturable structure that is attached to the end not passed through the all-suture anchoring element.

It is also an object of the present invention to provide a modified adjustable, locking all-suture anchor assembly including a hollow cylindrical mounting sleeve having an open distal end and an open proximal end defining a passageway therethrough.

The all-suture anchor assembly also includes a suture strand(s) and an all-suture anchoring element provided as part of the all-suture anchor assembly, so that when the all-suture anchoring element is grabbed by the end of a delivery inserter, both the all-suture anchoring element and the suture strand(s) threaded therethrough is placed into the bone channel during a tissue to bone repair.

It is another object of the present invention to provide a method for securing tissue to bone which includes passing the loose free end of the suture strand(s) through the all-suture anchoring element, and then enabling the suture strand(s) and all-suture anchoring element to be captured with an end of a delivery inserter. The other end of the suture strand(s) is captured or held by one end of the all-suture anchoring element. The all-suture anchoring element with the one end of the suture strand(s) that has been captured and the other end that has been passed through the all-suture anchoring element is inserted into a drilled bone channel or preferably a mounting sleeve in a drilled bone channel. The suture strand(s) that has been inserted into the bone channel or mounting sleeve along with the all-suture anchoring element in the bone channel is trapped when the all-suture anchoring element is deployed and the one end of the suture strand(s) that has been passed through the anchoring sleeve is exposed to allow drawing and securing of the tissue to the bone. Optionally, the length of the suture strand(s) can be adjusted, to effectuate a repair. Once inserted, the all-suture anchoring element of the all-suture anchor assembly holds the suture strand(s) in the bone channel directly or the sleeve placed into the bone channel along with the all-suture anchoring element. Alternatively, the length of the suture strand(s) can be adjusted by pulling on the free end suture or sutures.

It is another object of the present invention to provide a method for securing tissue to bone, wherein the assembly includes a cylindrical mounting sleeve which has an open proximal end and an open distal end defining a cylindrical passageway allowing access therethrough. The suture and all-suture anchoring element are then inserted into the sleeve contained in the bone channel.

Other objects and advantages of the present invention will become apparent from the following detailed description when viewed in conjunction with the accompanying drawings, which set forth certain embodiments of the invention.

DESCRIPTION OF THE PREFERRED EMBODIMENTS

Figure 1A:
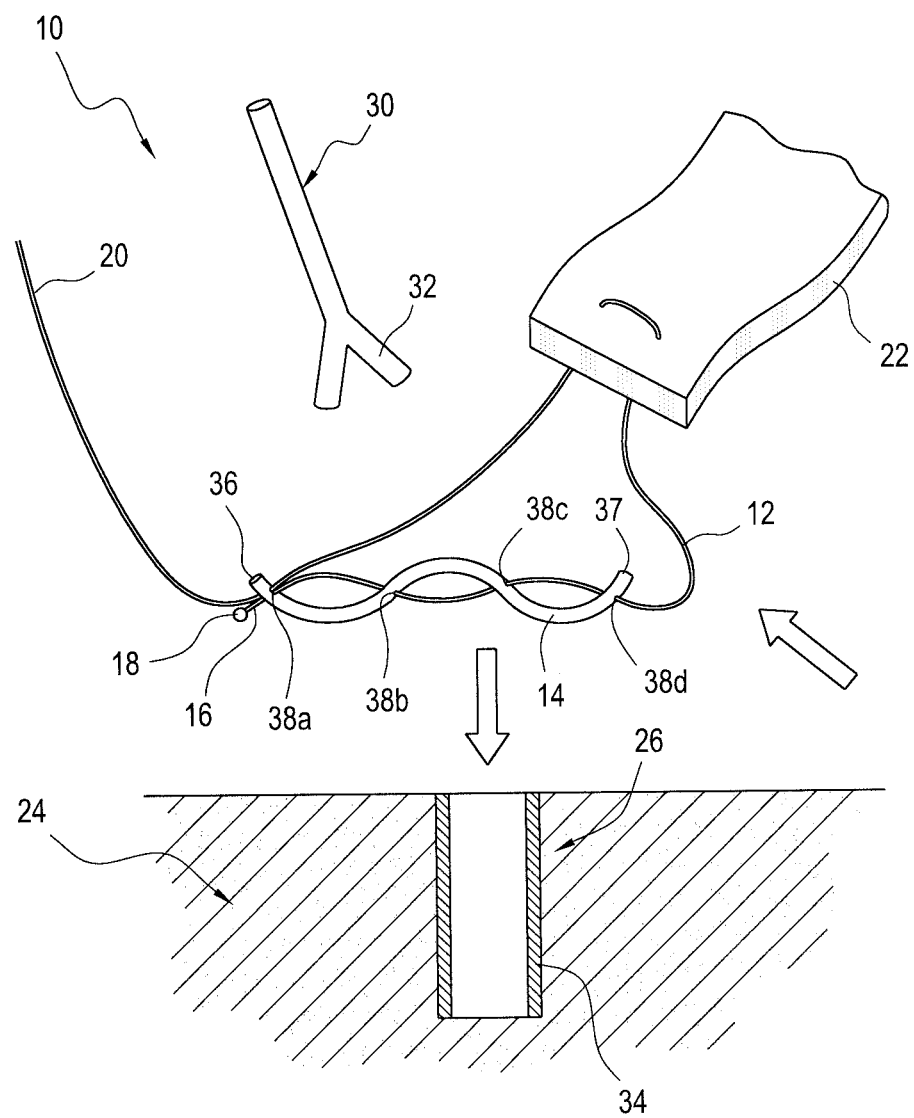
FIG. 1A shows the modified adjustable, locking all-suture anchor assembly where the free end of the suture strand(s) has been pulled through the tissue for subsequent engagement with the all-suture anchoring element of the all-suture anchor assembly by threading the free end therethrough for subsequent placement into a bone channel.
Figure 1B:
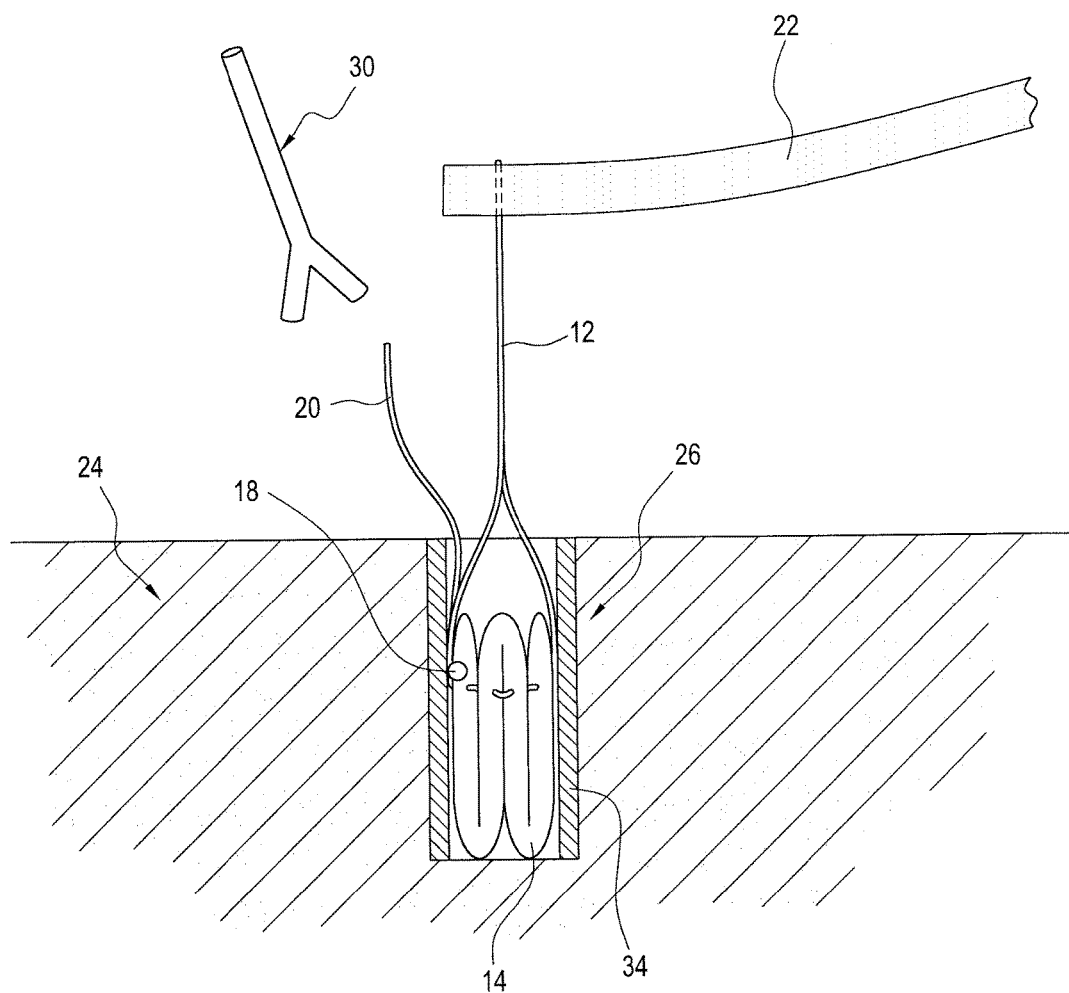
FIG. 1B shows the all-suture anchor assembly of FIG. 1A in its deployed state.
Figure 2A:
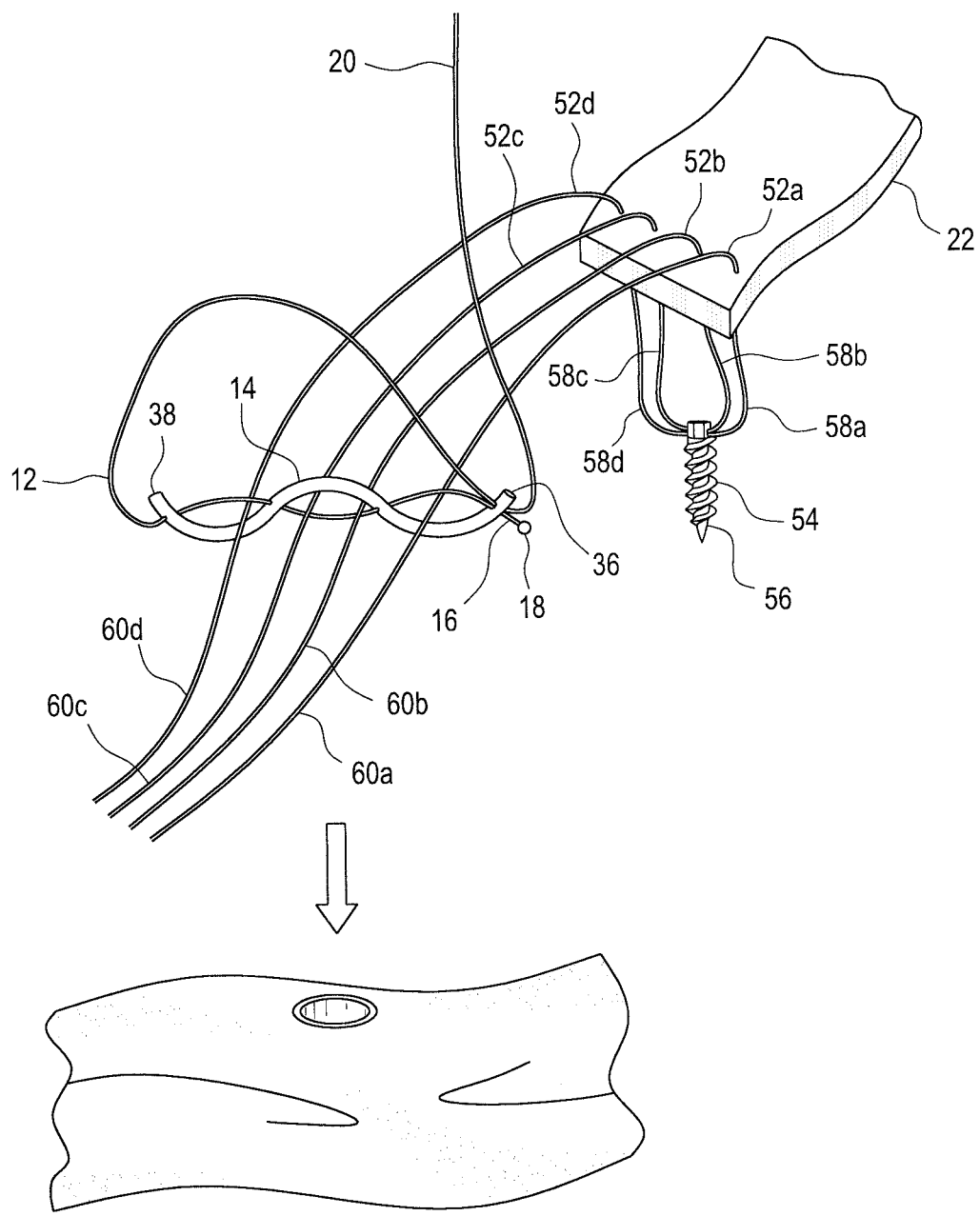
FIG. 2A shows the modified adjustable, locking all-suture anchor assembly employed in a dual row embodiment.
Figure 2B:
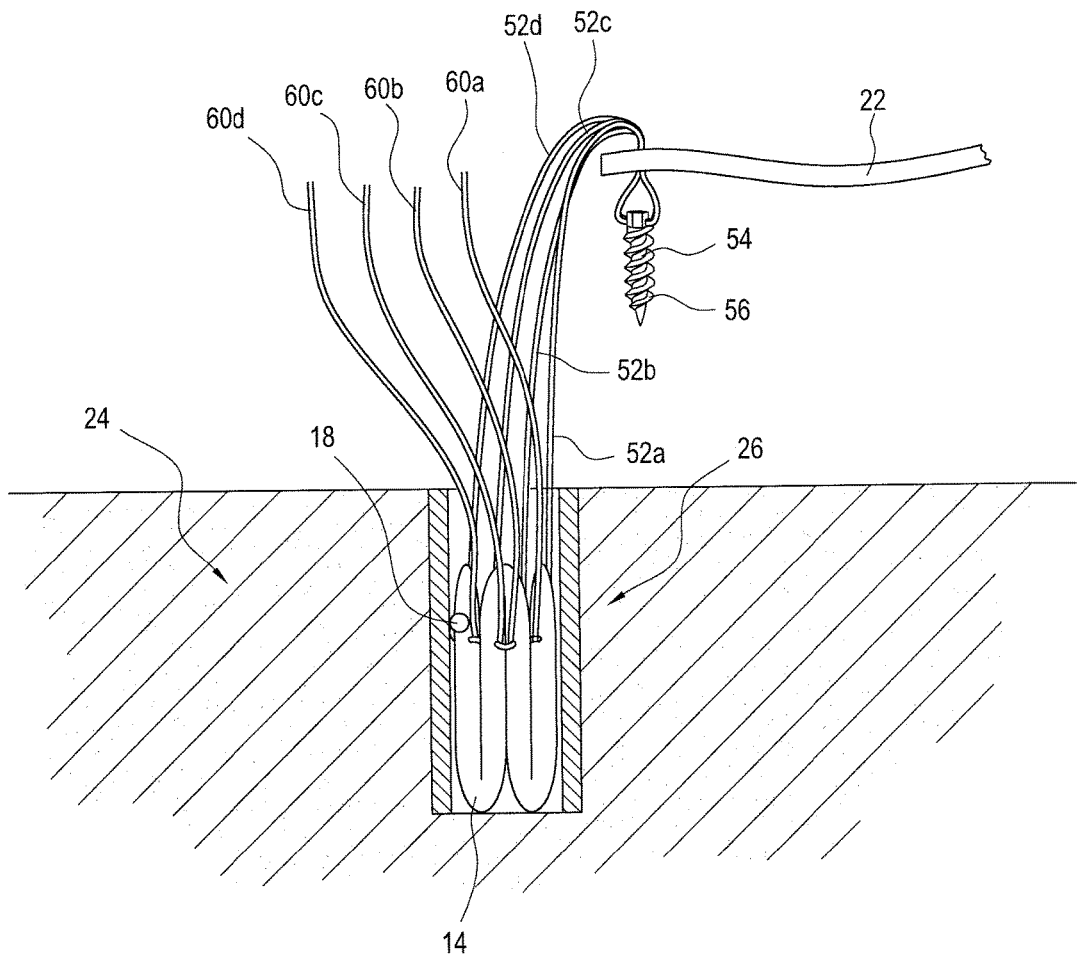
FIG. 2B shows the all-suture anchor assembly of FIG. 2A in its deployed state.

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as a basis for teaching one skilled in the art how to make and/or use the invention.

In accordance with the present invention, and with reference to FIGS. 1A, 1B, 2A, 2B, 3A, and 3B, a modified adjustable, locking all-suture anchor assembly 10 is disclosed. The modified adjustable, locking all-suture anchor assembly 10 includes at least one suture strand 12 and an all-suture anchoring element 14. The suture strand 12 has a suture first end 16 and a suture second end 20. The suture first end 16 includes a knot (bead, enlargement, or other capturable structure) 18, while the suture second end 20 is free and accessible for manipulation by a medical practitioner as will be discussed below in detail.

As will be described in greater detail below, the suture first end 16 is held in or by the all-suture anchoring element 14 through the inclusion of the knot 18. The knot functions to anchor the suture first end 16 in relation to the all-suture anchoring element 14 and retain the suture first end 16 in position relative to the all-suture anchoring element 14 when the suture second end 20 is pulled in accordance with the present invention. With the suture first end 16 held in position relative to the all-suture anchoring element 14, the suture second end 20 is threaded through the all-suture anchoring element 14 and is then passed through the tissue 22. The suture second end 20 is then once again passed through the all-suture anchoring element 14. The delivery inserter 30 is used to capture both the all-suture anchoring element 14 and the suture strand 12 threaded through the all-suture anchoring element 14, at least once, for insertion into a sleeve 34 in a bone channel 26. It is appreciated the inserter device 30 may capture both the all-suture anchoring element 14 and the suture strand 12 together or capture them separately.

As will be fully appreciated based upon the following disclosures, the present invention achieves secure attachment of soft tissue 22 to a bone mass 24 using the adjustable, locking all-suture anchor assembly 10. The suture strand 12, once threaded through the tissue 22, at least once, has its free suture second end 20 passed through an all-suture anchoring element 14 to allow the free second suture end 20 of the suture strand 12 to be threaded therethrough. It is also appreciated the suture strand 12 may be adjustable in length through the inclusion of a slip knot along the length of the suture strand 12. It is also appreciated that once the all-suture anchoring element 14 with the suture second end 20 threaded therethrough is inserted into the bone channel 26 by the inserter end 32, a surgeon can draw of the tissue 22 to the bone 24 by pulling of the suture second end 20 after the all-suture anchoring element 14 has been deployed or bunched.

In particular, the all-suture anchoring element 14 is preferably composed solely of an enlarged piece of cylindrical suture material or a suture tape. The enlarged surface area of the all-suture anchoring element 14 allows for the passage of the suture strand 12 therethrough in a manner providing for entanglement of the all-suture anchor element 14 and the suture strand 12. The suture anchor element 14 includes a first end 36 and a second end 37, as well as a thickness, a width and a length along a longitudinal axis. It is appreciated the all-suture anchoring element may optionally makes use of barbs or similar grasping features along its length. One particular type of barb is a one-way type barb mechanism which grips the suture ends and prevents the sutures from backing out of the entanglement of the all-suture anchoring element.

As briefly mentioned above, the all-suture anchor assembly 10 includes the suture strand 12, which is passed through the all-suture anchoring element 14 at various locations along the length of the all-suture anchoring element 14. That is, the suture penetrates and traverses the all-suture anchoring element 14 so as to define apertures in the all-suture anchoring element 14. The intersections of the suture with the all-suture anchoring element 14 are referred to herein as suture aperture locations 38a-d and, as such, each of the suture aperture locations 38a-d is a location where the suture strand 12 passes through the thickness of the all-suture anchoring element 14. As shown in FIG. 1A, there are four suture aperture locations 38a-d. It is appreciated that as few as three suture aperture locations on a particular all-suture anchor assembly may function well. Similarly, more suture aperture locations may be provided, although it has been discovered that each additional suture aperture location increases friction against the suture thus reducing a surgeon's ability to slide the suture in relation to the all-suture anchoring element 14. While the suture aperture locations 38a-d disclosed above in accordance with a preferred embodiment are all centrally located along the all-suture anchoring element 14 so as to be oriented along the central longitudinal axis of the all-suture anchoring element 14, it is appreciated the suture aperture locations 38a-d may be varied (for example, staggered on opposite sides of the central longitudinal axis of the all-suture anchoring element 14) without departing from the spirit of the present invention. In accordance with a preferred embodiment, the all-suture anchoring element 14 may have various length and width dimensions depending upon the purpose for which it is intended.

With the foregoing in mind, it is appreciated that a large variety of constructions and materials will work for the all-suture anchor assembly 12. It has been discovered that for each type of construction (i.e., braided, woven, non-woven, or knitted) there is an advantage for using a material that increases in width for every reduction in length. This advantage provided for increased diameters for a particular number of folds, pleats, crinkles or other changes in the shape of the all-suture anchor element 14. Regardless of the material chosen for use in accordance with the present invention, the material must exhibit desirable deformation and retention characteristics.

In accordance with the present method, the free suture second end 20 of the suture strand 12 is first passed through the all-suture anchoring element 14 at various locations along the length of the all-suture anchoring element so as to define the suture aperture locations 38a-d along the length of the all-suture anchoring element 14. As the suture strand 12 is pulled through the all-suture anchoring element 14, the suture first end 16 of the suture strand 14 is captured or blocked from passing through the first suture aperture location 38a by way of the knot 18 formed at the suture first end 16 of the suture strand 12. In particular, the knot 18 is of such a size that it will not pass through the aperture formed by the passage of the suture second end 20 and defining the first suture aperture location 38a. As the first suture aperture location 38a is found at the first end 36 of the all-suture anchor element 14, and as will be appreciated based upon the following disclosure, the blockage of the suture first end 36 allows for folding, bunching or crinkling of the all-suture anchor element 14 as the second end 37 of the all-suture anchor element 14 is drawn toward the first end 36 of the all-suture anchor element 14.

Once the free suture second end 20 of the suture strand 12 completes its passage through the all-suture anchoring element 14, the free suture second end 20 of the suture strand 12 is passed, at least once, through the soft tissue 22 one wishes to secure to a bone mass 24. The free suture second end 20 of the suture strand 12 is then threaded once again through the all-suture anchoring element 14 and frictionally retained therein (or grabbed by barbs or gripping features located on the all-suture anchor element). In accordance with a preferred embodiment, the free suture second end 20 of the suture strand 12 is threaded through the all-suture anchoring element 14 at the first suture aperture location 38a or at a location adjacent to the first suture aperture location 38a. By passing the free suture second end 20 of the suture strand 12 through the all-suture anchoring element 14 at a position adjacent to the knot 18 at the suture first end 16, friction is created that assists in holding the all-suture anchoring element 14 in its compressed state.

It is appreciated that if suture strand 12 is relatively long, it may be constructed so as to allow for adjustment in length. Once the free suture second end 20 of the suture strand 12 has been threaded through the all-suture anchoring element 14, the all-suture anchoring element 14 is inserted by an inserter end 32 of a delivery inserter 30 into a previously formed bone channel 26 in manner causing deployment or expansion of the all-suture anchoring element 14 in the bone channel 26.

The inserter device 30 is operated by a surgeon whereby he captures the all-suture anchoring element 14 and the suture strand 12. The surgeon inserts both the all-suture anchoring element 14 and the entangled portion of the suture strand 12 in the bone channel 26 by pushing the inserter end 32 of the delivery inserter 30 into the bone channel 26. At that point, the surgeon can push a button or turn a device on the delivery inserter 30 which enables the deployment of the all-suture anchor element 14. The delivery inserted 30 may then be removed. As explained above, this manipulation causes the all-suture anchoring element 14 to fold, bend, crease, crinkle, bunch or otherwise change shape in a manner that compresses the all-suture anchoring element 14 in a manner that ultimately increases the size of the all-suture anchoring element 14 in a direction substantially perpendicular to the longitudinal axis of the bone channel 26 to develop an outwardly directed forced that is directed at the walls of the bone channel 26.

Figure 4A:
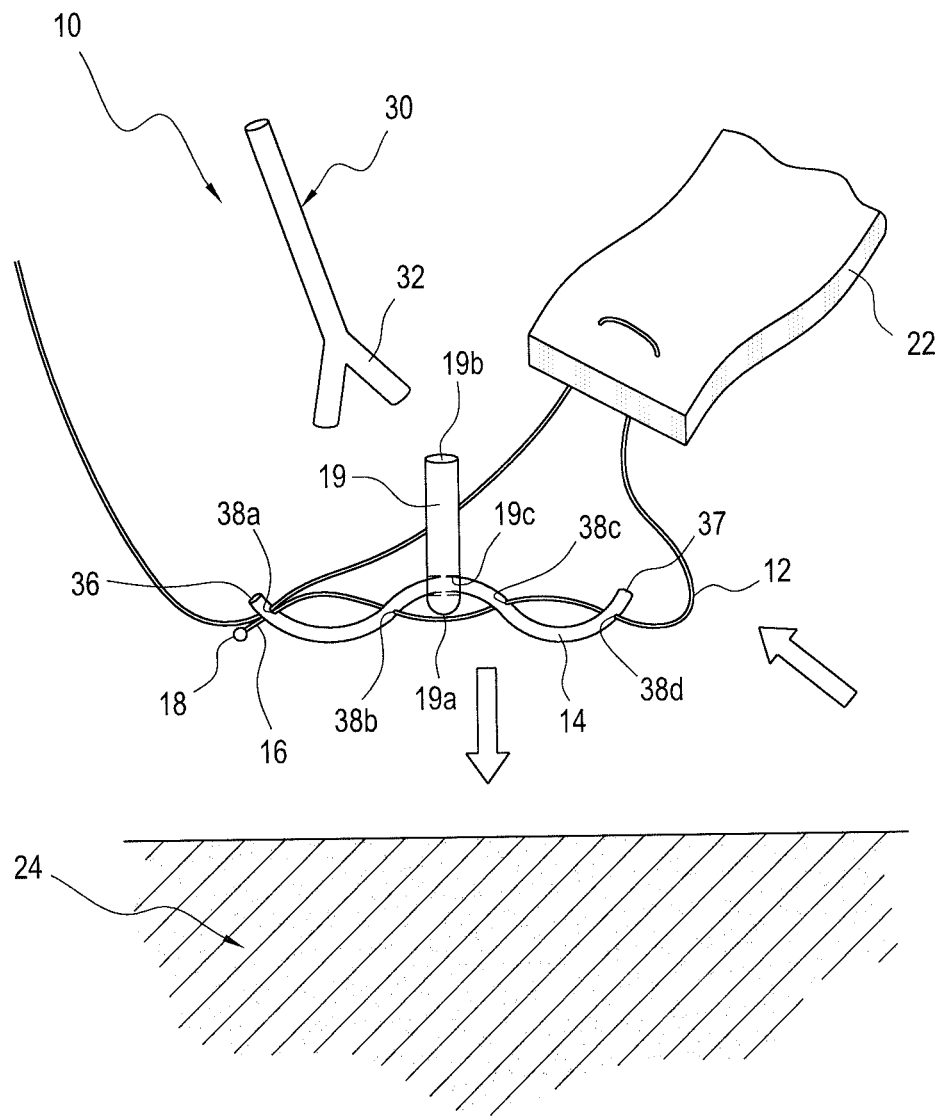
FIG. 4A shows an alternate embodiment of the all-suture anchor assembly.
Figure 4B:
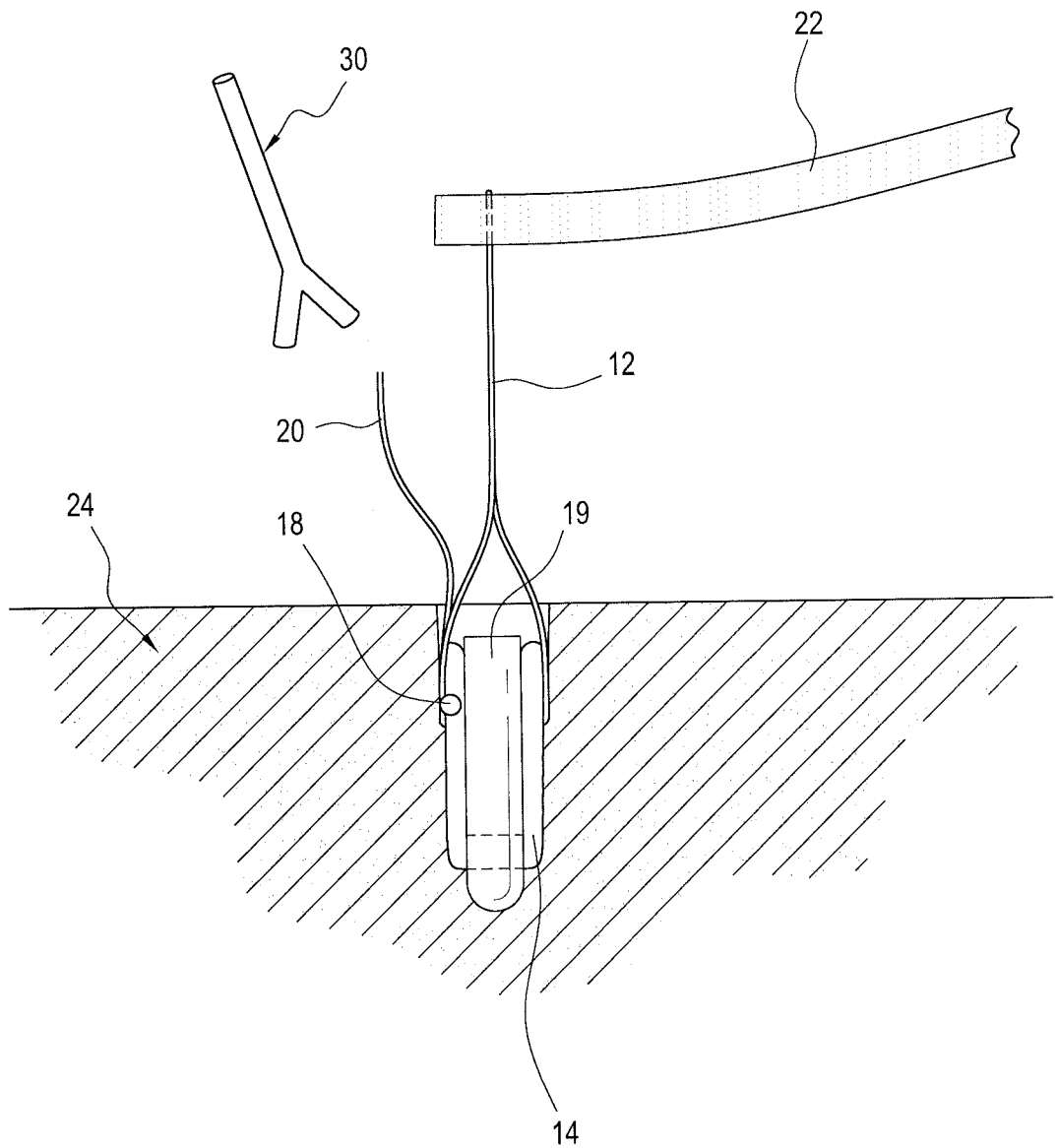
FIG. 4B shows the all-suture anchor assembly of FIG. 4A in its deployed state.
Figure 5A:
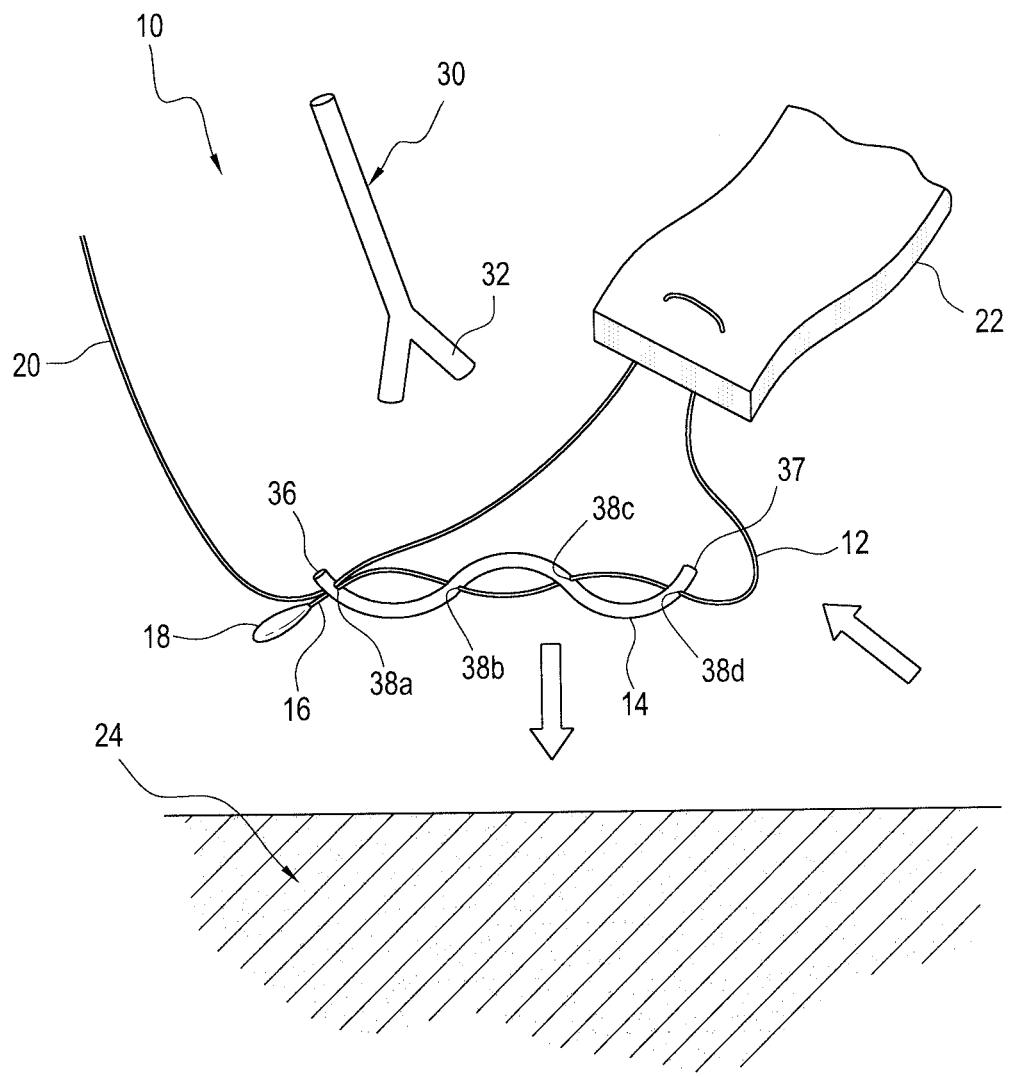
FIG. 5A shows another alternate embodiment of the all-suture anchor assembly.
Figure 5B:
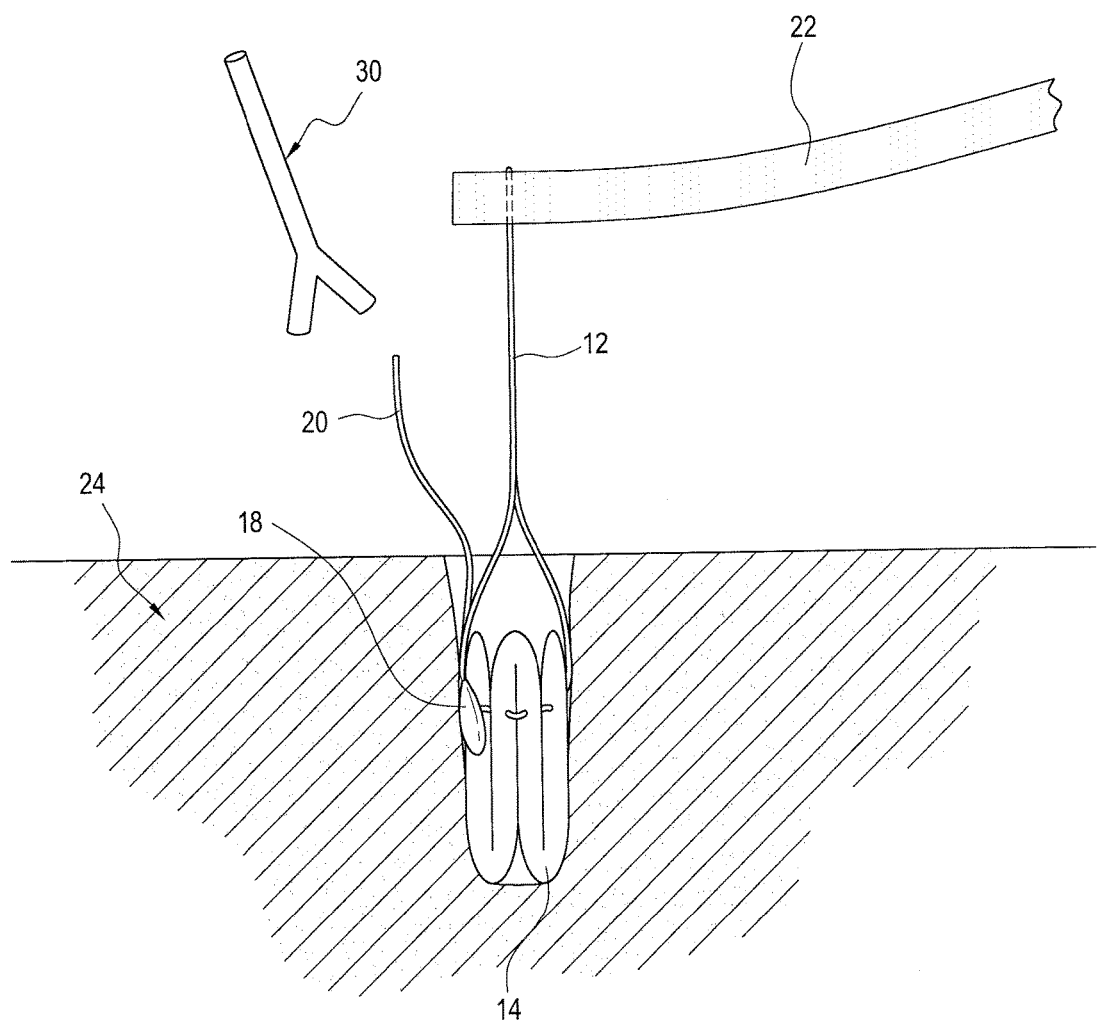
FIG. 5B shows the all-suture anchor assembly of FIG. 5A in its deployed state.

Referring to FIGS. 4A and 4B, it is further contemplated the all-suture anchor assembly 10 may be supplemented with the inclusion of a solid polymer tip member 19 that is integrated onto the all-suture anchoring element 14 for the purpose of enhancing the surgeon's ability to position the all-suture anchor assembly 10 within the bone mass 24. In accordance with a preferred embodiment, the solid tip member 19 is cylindrical in shape and includes a forward first end 19a and a rear second end 19b. The forward first end 19a is semispherical in shape to enhance penetration as the tip member 19 is forced into bone 104 as discussed below. The tip member 19 is preferably secured to the all-suture anchoring element 14 by passing the all-suture anchoring element 14 through a lateral aperture 19c formed at the forward first end 19a of the tip member 19. Functionality in conjunction with the tip member 19 may be further enhanced by the provision of spikes or ridges along the outer surface thereof. Other than the inclusion of the tip member 19 along the length of the suture anchor 16, the structure, function, and operability of the all-suture anchor assembly 10 will remain the same. Still further, and with reference to FIGS. 5A and 5B, the knot 18 could be enlarged to function in a manner similar to the solid tip member.

As shown, and further to the discussion above, the suture strand 12 and the all-suture anchoring element 14 are installed in an elongated fashion to take advantage of a small diameter configuration, referred to herein as an undeployed state or installation state. Deployment occurs as the delivery inserter 30 is manipulated and the suture strand 12 is tensioned causing the all-suture anchoring element 14 to fold, bend, crease, crinkle, bunch or otherwise change shape in a manner that compresses the all-suture anchoring element 14. It is appreciated deployment may occur before, after, or as the delivery inserter is removed. As the all-suture anchoring element 14 is compressed in this manner it ultimately increases in size in a direction substantially perpendicular to the longitudinal axis of the bone channel 26 (or otherwise oriented to contact side walls of the bone channel 26) and develops an outwardly directed forced that is directed at the walls of the bone channel 26. As such, and when tension is no longer being applied by the delivery inserter, or other delivery instrument, the all-suture anchoring element 14 exhibits an outward bias resulting in expansion of the all-suture anchoring element 14 in a direction substantially perpendicular to the longitudinal axis of the bone channel 26 (or otherwise oriented to contact side walls of the bone channel 26) into which it is positioned, resulting in frictional engagement or gripping the wall of the cancellous bone, which is referred to herein as the expanded deployed state.

The all-suture anchoring element 14 is folded or otherwise compressed to form pleats between adjacent suture aperture locations. This pleating reduces the distance between the first suture aperture location and the second suture aperture location, as measured along the length of the suture anchor. These pleats form a bunched mass of suture material effectively increasing a diameter, or cross sectional dimension, (as measure in relation to the axis of the bone channel 26) of the all-suture anchoring element 14, which ultimately causes the all-suture anchor assembly 10 to displace cancellous bone. The relative increase in the cross sectional size of the all-suture anchoring element 14 in the direction substantially perpendicular to the longitudinal axis of the bone channel 26 (or in another direction to facilitate contact of the all-suture anchoring element 14 with the side walls of the bone channel 26) creates a retention force of the all-suture anchor assembly 10.

It is appreciated a mechanical tensioning mechanism, as is well known to those skilled in the art, may be used during the deployment of the all-suture anchoring element. Such mechanical tensioning mechanisms pull or ratchet the suture while the delivery inserter holds the all-suture anchoring element in place. Mechanical tensioning, of this nature, may be preferable as this can more tightly 'fold' or 'bunch' the all-suture anchoring element, thereby increasing the created tension, that is, the outward force of the all-suture anchoring element, which is relative to the longitudinal axis of the bone channel and toward the walls of the bone channel, resulting from increased compression of the all-suture anchoring element. The changed shape of the all-suture anchoring element provides security within the bone, for example, below the cortical layer.

With the all-suture anchoring element 14 securely held within the bone channel 26, the free second suture end 20 may be pulled to draw the tissue 22 to the bone 24. Because the first suture end 16 is blocked by the knot 18, pulling upon the second suture end 20 acts to draw the tissue 22 toward the bone channel 26 without pulling the first suture end 16 through the all-suture anchoring element 14. In fact, the first suture end 16 is effectively fixed in position relative to the all-suture anchoring element 14.

It should be appreciated that the relative fit of the all-suture anchor assembly in the bone channel 26 is shown as being relatively "loose." This is done to provide for a clear view for the elements making up the present invention. In practice, it is appreciated that the suture, all-suture anchoring element 14, and delivery inserter would be tightly pressed into the bone channel 26, as any excess space would need to be taken up by the expansion of the all-suture anchor assembly in a direction substantially perpendicular to the longitudinal axis of the bone channel 26 (or otherwise oriented to contact side walls of the bone channel 26).

In accordance with a preferred embodiment, a sleeve 34 is used to enhance to anchoring of the all-suture anchoring element 14 within the bone channel 26. It is appreciated that various sized mounting sleeves 34 may be used and the mounting sleeve 34 defines a hollow cylindrical body with a central passageway. The mounting sleeve 34 includes a distal end and a proximal end, and the mounting sleeve 34 is open, or hollow, as it extends from the distal end thereof to the proximal end thereof allowing access below the mounting sleeve 34 to the internal bone mass 20. The hollow cylindrical mounting sleeve 34 provides an anchor recess (or central passageway) extending from the proximal end of the hollow cylindrical mounting sleeve 34 to the distal end of the hollow cylindrical mounting sleeve 34. The central passageway, in the hollow cylindrical mounting sleeve 34, allows for capture of the combination of the all-suture anchoring element 14, along with the suture strand 12, when they are both placed within the central passageway and then expanded as described above so as to create tension is created by the bunching into the central passageway by an inserter end 32.

The sleeve 34 is positioned within the bone channel 26 prior to insertion and compression of the all-suture anchoring element as described above. One goal of such the sleeve 34 is to enhance fixation of the all-suture anchoring element 14 by creating an interaction between the sleeve 34 and the all-suture anchoring element 14 that is frictionally more stable than that achieved by the direct interaction of the all-suture anchoring element 14 with the bone. While a screw-in method of sleeve insertion (that is, the sleeve 34 includes threads along its outer surface that engage with the bone during insertion) is contemplated in accordance with a preferred embodiment, the sleeve may also be pressed into position or deployed in some other manner. The sleeve need not be uniform, so long as it can be secured within the bone channel 26, likely along the perimeter thereof. Alternatively, sleeve 34 may be deployed within the bone channel 26 such that space exists between the bottom of the bone channel 26 and the bottom of the sleeve, thereby providing space allowing for the all-suture anchoring element 14 to change shape 'distal' to the sleeve 34 thereby providing fixation. It is appreciated the sleeve 34, in accordance with a preferred embodiment of the present invention, would be positioned in the cortical bone aspect of the bone channel 26, but could also extend into the cancellous bone. It is, however, appreciated the sleeve could be slightly protruding and not flush with the cortical surface, or it could be placed below the cortical surface, as long as it is well-fixed. It is also appreciated that when the all-suture anchoring element 14 is deployed distal to the sleeve 34, that is, between the sleeve 34 and the bottom of the bone channel 26, fixation doesn't require 'force'. Rather, the enlargement and increased size (in a direction toward the walls of the bone channel 26) of the all-suture anchoring element 14 upon deployment, distal to the sleeve 34 after insertion, prevents the all-suture anchoring element 14 from backing out of the sleeve 34 (and ultimately from backing out of the bone channel 26).

Although a single hole repair is described above, it is appreciated that more extensive repairs can comprise multiple drilled bone channels. When multiple drilled bone channels are used, multiple adjustable, locking all-suture anchor assembly repair assemblies are used. Each assembly is used as described above and inserted into a separate drilled bone channel or a mounting sleeve placed in the drilled bone channel. This enables a surgeon to grab various sections of a tissue and draw the tissue to bone at several locations to secure the tissue for a repair.

FIGS. 2A, 2B, 3A and 3B depict use of the adjustable, locking all-suture anchor assembly 10, described above with reference to FIGS. 1A and 1B, in conjunction with a plurality of sutures 52*a-d* that have been combined and a bone anchor 54 (or knot). The plurality of sutures 52*a-d* are passed through the tissue 22 and then threaded through a loop 30 formed by passing the free suture second end 20 of the suture strand 12 through the all-suture anchoring element 14 for subsequent bunching with the all-suture anchoring element 14 when inserted into a sleeve 34 in a bone channel 26.

In accordance with the embodiments disclosed with reference to FIGS. 2A, 2B, 3A and 3B, a dual row surgical procedure is contemplated. In addition to the elements of the all-suture anchor assembly 10 disclosed above with regard to the embodiment of FIGS. 1A and 1B, the embodiments of FIGS. 2A, 2B, 3A and 3B use a tissue coupling suture assembly 50 with a bone anchor 54 and a plurality of sutures 52*a-d*. The tissue coupling suture assembly 50, therefore, includes the bone anchor 54 that has an anchor body 56. The anchor body 56 has traditional threads for attachment of the anchor body 56 to bone in a manner known to those skilled in the art. While an embodiment employing a traditional anchor is disclosed, it is appreciated various anchoring systems may be employed, including, but not limited to, wedge shaped, spikes, prongs, threads, or all-suture. In fact, and as will be explained below in greater detail, the all-suture anchor assembly described above may be employed as a replacement for the traditional bone anchor described above and, as such, the all-suture anchor assembly 10 may be employed in securing the tissue coupling suture assembly 50 to bone.

A plurality of sutures 52*a-d* extend from and are secured to the anchor body 56, wherein each of the sutures 52*a-d* includes a first end 58*a-d* secured to the anchor body 56 and a second end 60*a-d* that is ultimately coupled with the all-suture anchor assembly 10. In this way, and as will be appreciated based upon the following disclosure, the present all-suture knodess repair system is particularly well suited for extending the plurality of sutures 52 between anchored locations defined by the bone anchor 54 and the all-suture anchor assembly 10, with tissue held therebetween, wherein the anchor body 56 fixedly secures the first ends 58*a-d* of the plurality of sutures 52*a-d* at one location and the all-suture anchor assembly 10 secures the second ends 60*a-d* of the plurality of sutures 52 at a second location. In this way, the present all-suture knotless repair system is especially well adapted for creating a "dual-row" repair. However, it is also appreciated a variety of other uses and techniques may be implemented within the spirit of the present invention.

With regard to the attachment of the first ends 58*a-d* of the plurality of sutures 52 to the anchor body 56, the first ends 58*a-d* may be secured to the anchor body 56 in a fixed manner or in a sliding manner, both of which are well known to those skilled in the art. While the disclosed embodiment shows four lengths of suture, each having one end fixed to the anchor body, other configurations are contemplated. For example, one or more of the sutures may be slidable with respect to the anchor body. In some embodiments, the sutures and/or suture anchor may be configured to be moved relative to the anchor body and then fixed either by a knot or other technique. In other embodiments, the slidable suture may become fixed while the anchor is inserted into bone, such as by compressing the suture between the side of the anchor and the bone.

With regard to the attachment of the second ends 60*a-d* of the plurality of sutures 52*a-d* to the all-suture anchor assembly 10, the second ends 60*a-d* are passed between the suture strand 12 and the all-suture anchoring element 14 in manner creating friction that holds the second ends 60*a-d* of the plurality of sutures 52*a-d* relative to the all-suture anchor assembly 10. In accordance with a first embodiment and with reference to FIGS. 2A and 2B, the second ends 60*a-d* of the plurality of sutures 52*a-d* are positioned between the suture aperture locations 38*a-d* such that when the all-suture anchor assembly 10 is contracted to its compressed state as discussed above, the friction of the compressed all-suture anchoring element 14 fixedly secures the second ends 60*a-d* of the plurality of sutures 52*a-d* relative to the all-suture anchor assembly 10.

Figure 3A:
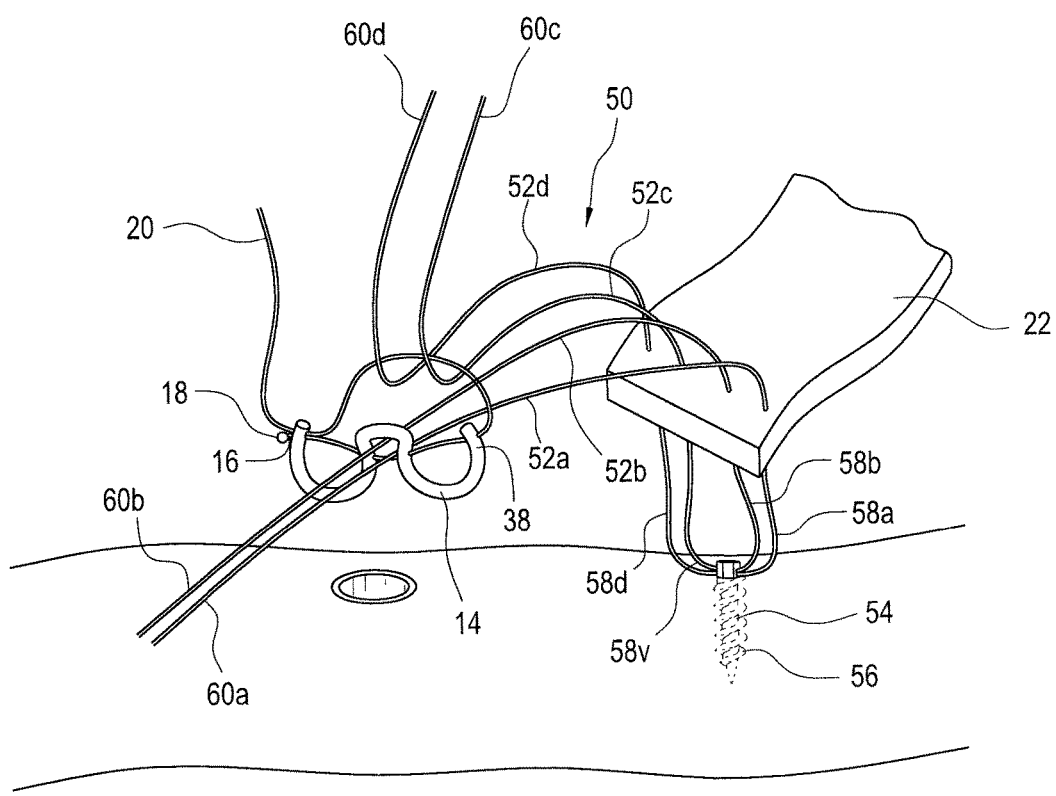
FIG. 3A shows an alternative to the modified adjustable, locking all-suture anchor assembly employed in a dual row embodiment as disclosed in FIGS. 2A and 2B.
Figure 3B:
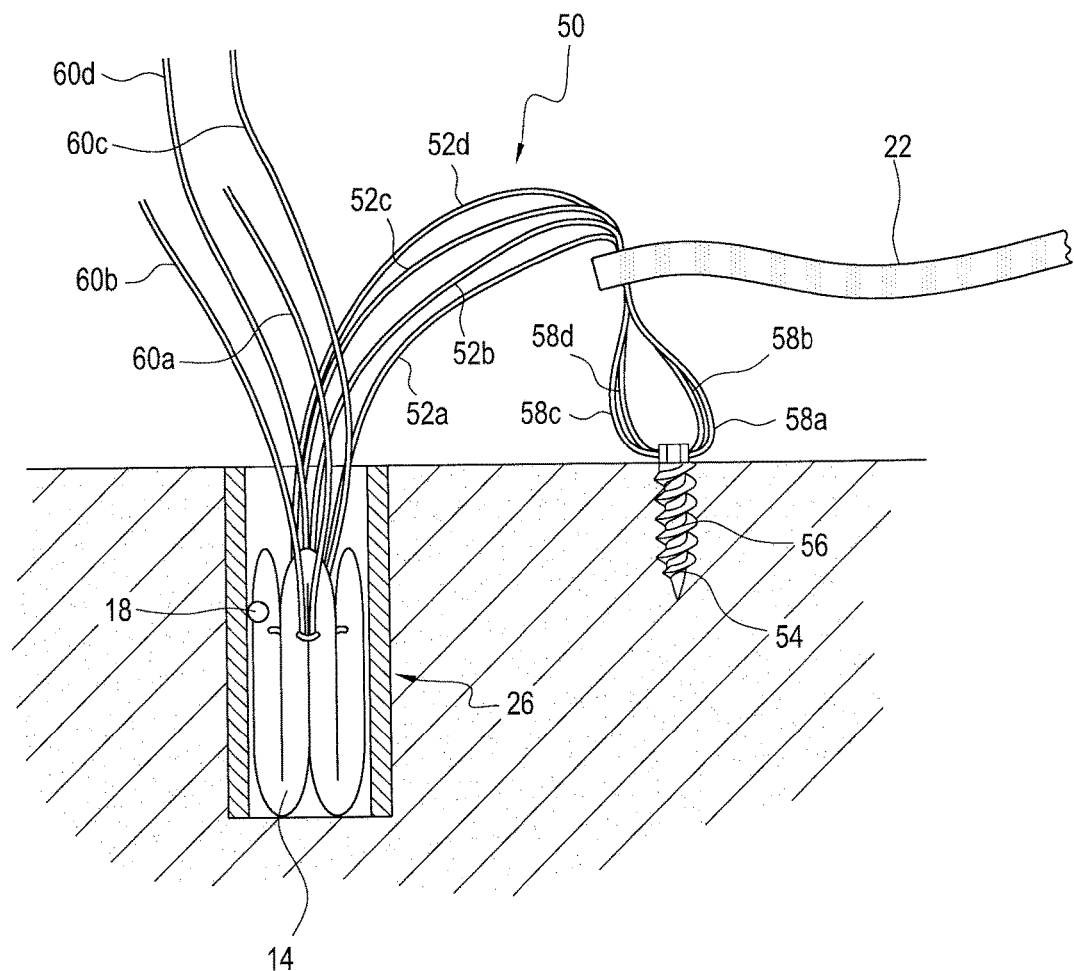
FIG. 3B shows the all-suture anchor assembly of FIG. 3A in its deployed state.

In accordance with a second embodiment and with reference to FIGS. 3A and 3B, the second ends 60*a-d* of the plurality of sutures 52*a-d* are split and two of the plurality of sutures 52*a*, 52*b* are positioned between the suture aperture locations 38*a-d* such that when the all-suture anchor assembly 10 is contracted to its compressed state as discussed above, the friction of the compressed all-suture anchoring element 14 fixedly secures the second ends 60*a-d* of the plurality of sutures 52*a-d* relative to the all-suture anchor assembly 10. The other two of the plurality of sutures 52*c*, 52*d* are positioned within the loop defined by the suture strand 12 as the suture second end 20 and the suture first end 16 pass through the all-suture anchoring element 14. As such, and as with the two of the plurality of sutures 52*a*, 52*b* are positioned between the suture aperture locations 38*a-d*, the two of the plurality of sutures 52*c*, 52*d* are positioned within the loop are fixedly secured relative to the all-suture anchor assembly 10 upon folding, bunching or otherwise crinkling the all-suture anchor element 14. As such, and whether the all-suture anchor element 14 is folded, bunched or otherwise crinkled within a bone channel 26 or at another location within the body, friction is created between the second ends of the plurality of sutures 52*a-d* and the all-suture anchor assembly 10 in a manner securing the second ends 60*a-d* of the plurality of sutures 52*a-d* to the all-suture anchor assembly 10.

In particular, the embodiments are FIGS. 2A, 2B, 3A and 3B are practiced in the following manner. Once the all-suture anchor assembly 10 is formed with the suture second end 20 and the suture first end 16 passing through the all-suture anchoring element 14 to form a loop, the plurality of sutures 52*a-d* are first passed through the tissue to be attached. Thereafter, the second ends 60*a-d* of the plurality of sutures 52*a-d* are passed between the suture strand 12 and the all-suture anchoring element 14 in either the manner disclosed with reference to FIGS. 2A and 2B or the manner disclosed with reference to FIGS. 3A and 3B. The all-suture anchor assembly 10, in particular, the all-suture anchoring element 14 and the suture strand 12 are then inserted into the bone channel 26 as discussed above with regard to the embodiment disclosed with reference to FIGS. 1A and 1B. In practice, and as discussed above in greater detail, it is appreciated that the suture strand 12, all-suture anchoring element 14, and delivery inserter 30 are tightly pressed into the bone channel 26, and the free suture second end 20 is pulled, causing the all-suture anchoring element 14 to fold, bend, crease, crinkle, bunch or otherwise change shape in a manner that compresses the all-suture anchoring element 14 in a manner that ultimately increases in size in a direction substantially perpendicular to the longitudinal axis of the bone channel 26 (or otherwise oriented to contact side walls of the bone channel 26) and develops an outwardly directed forced that is directed at the walls of the bone channel 26.

Prior to expansion and folding (or otherwise changing the shape) of the all-suture anchoring element 14, the second ends 60a-d of the plurality of sutures 52a-d are tensioned as desired. With the sutures 52a-d tensioned, the suture strand 12 is tensioned (either by manually or mechanically pulling this suture) to cause the all-suture anchoring element 14 to fold and expand as explained above. In addition to causing the all-suture anchoring element 14 to grip the wall of the cancellous bone channel 26, the tensioning of the suture and the resulting folding of the all-suture anchoring element 14 causes the frictional engagement between the all-suture anchor assembly 10 and the second ends 60a-d of the plurality of sutures 52a-d. In particular, and as the all-suture anchoring element 14 is compressed during the deployment process, the all-suture anchoring element 14, the suture and the plurality of sutures 52a-d are brought closer together in a tightly compacted and entangled configuration that effectively creates a unitary mass that ultimately prevents the sutures 52a-d from being pulled away from the all-suture anchoring element 14.

As briefly mentioned above, it is contemplated the conventional anchor body 56 secured to the first ends of the sutures may be replaced with a second all-suture anchor assembly 10 as described above. In accordance with such an embodiment, the all-suture anchor assembly 10 of the present invention would be used in fixedly securing both the first and second ends of the sutures to the bone or other body part being secured.

Where the all-suture anchor assembly 10 including a solid tip member 19, or enlarged knot 18, as discussed above with reference to FIGS. 4A, 4B, 5A and 5B is employed, the methodology may be altered considering a bone channel may not be required, and the solid tip member 19 may be used to penetrate the bone mass 24 and form a cavity into which the all-suture anchor assembly 10 is positioned. In accordance with such an embodiment, and with the delivery inserter 30 directly attached to the solid tip member 19, the forward first end 19a of the solid tip member 19 is impacted directly into bone mass 24, with the remainder of the solid tip member 19 following and being inserted into the bone mass 24. Thereafter, the all-suture anchoring element 14 and the anchor suture strand 12 are forced into the hole created by the solid tip member 19, and the all-suture anchoring element 14 is folded, bent, creased, crinkled, bunched or otherwise changed in shape in a manner that compresses the all-suture anchoring element 14 as discussed above. Other than the inclusion of the solid tip member 19 and the direct impacting into the bone mass 24, the methods for use disclosed herein remain the same.

The all-suture knotless repair system described above may be employed in a variety of medical procedures. Included amongst those medical procedures that may take advantage of the present all-suture knotless repair system are those procedures disclosed in U.S. Patent Application Publication No. 2015/0216522, entitled "SUTURE ANCHOR," published Aug. 6, 2015, which is incorporated herein by reference. Briefly, and considering the procedures disclosed in the '522 publication, it is important to note that 1) one or more medial row anchors can be used; 2) one or more lateral row anchors can be used; and 3) all, or only some, of the sutures from one medial row anchor can be linked to one, or more than one, lateral row anchor (therefore, sutures form multiple medial row anchors may be crossed to multiple lateral row anchors).

In many situations throughout the discussion above, the terminology relating to the secure attachment of soft tissue to bone mass has been used. Such terminology refers to the attachment or reattachment of tissue to a bone mass by securely binding the tissue to the bone mass utilizing the novel knotless suture anchor assembly. The suture element can be made up of a known suture material, or it can be made of polymer materials, or can be formed of bioabsorbable/biocomposite material such as a polylactide polymer.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. An adjustable, locking all-suture anchor assembly, comprising:
   at least one suture strand, the at least one suture strand has a suture first end and a suture second end, wherein the suture first end includes an enlarged capturable structure and the suture second end is free and accessible for manipulation by a medical practitioner;
   an all-suture anchoring element; and
   a tissue coupling suture assembly composed of a plurality of sutures and an anchor, second ends of the plurality of sutures are passed between the at least one suture strand and the all-suture anchoring element in manner creating friction that holds the second ends of the plurality of sutures relative to the all-suture anchor assembly;
   wherein the suture first end is held in or by the all-suture anchoring element through inclusion of the enlarged capturable structure and the enlarged capturable structure functions to anchor the suture first end in relation to the all-suture anchoring element and retain the suture first end in position relative to the all-suture anchoring element when the suture second end is pulled.

2. The all-suture anchor assembly according to claim 1, wherein the all-suture anchoring element is composed of an enlarged piece of cylindrical suture material or a suture tape.

3. The all-suture anchor assembly according to claim 1, wherein the at least one suture strand is passed through the all-suture anchoring element in a manner providing for entanglement of the all-suture anchor element and the suture strand.

4. The all-suture anchor assembly according to claim 3, wherein the at least one suture strand penetrates and traverses the all-suture anchoring element so as to define apertures in the all-suture anchoring element, and intersections of the at least one suture strand with the all-suture anchoring element are suture aperture locations.

5. The all-suture anchor assembly according to claim 1, further including a sleeve enhancing anchoring of the all-suture anchoring element within a bone channel.

6. The all-suture anchor assembly according to claim 1, where a number of the plurality of sutures are passed between the suture strand and the all-suture anchoring element in manner creating friction that holds the second ends of the plurality of sutures relative to the all-suture anchor assembly.

7. The all-suture anchor assembly according to claim 6, where the remaining plurality of sutures are positioned within a loop defined by the suture strand.

* * * * *